United States Patent [19]

Smith et al.

[11] 4,126,167

[45] Nov. 21, 1978

[54] GASTRIC TUBE DRAINAGE BAG

[75] Inventors: J. Weston Smith, St. Cloud; David J. Gottwalt, Rush City, both of Minn.

[73] Assignee: Patient Care Products, Inc., Burnsville, Minn.

[21] Appl. No.: 747,498

[22] Filed: Dec. 6, 1976

[51] Int. Cl.² ............................................. B65D 33/16
[52] U.S. Cl. ................................................. 150/8
[58] Field of Search .................. 150/8; 128/214 D; 215/247, 277, 317, 306

[56] References Cited

U.S. PATENT DOCUMENTS

| 2,838,768 | 6/1958 | Fischett | 150/8 |
|---|---|---|---|
| 3,209,752 | 10/1965 | Bujan | 150/8 |
| 3,537,109 | 11/1970 | Spurrier | 150/8 |
| 3,788,374 | 1/1974 | Saijo | 150/8 |
| 3,915,212 | 10/1975 | Bujan | 150/8 |
| 4,005,739 | 2/1977 | Winchell | 150/8 |
| 4,049,034 | 9/1977 | Vcelka | 150/8 |

FOREIGN PATENT DOCUMENTS 2,307,712 4/1976 France ................................. 150/8

*Primary Examiner*—Ro E. Hart
*Attorney, Agent, or Firm*—Paul L. Sjoquist

[57] ABSTRACT

Apparatus and a process for its manufacture is disclosed for constructing a gastric tube drainage bag from two plastic parts, wherein one part comprises a thin bag having a seal at one end and the second part comprises a nozzle and cap assembly formed from a single plastic part, which assembly has a tapered base for insertion into the open bag end, against which the bag end may be sealed by a heating process.

2 Claims, 5 Drawing Figures

GASTRIC TUBE DRAINAGE BAG

BACKGROUND OF THE INVENTION

In a hospital environment it is frequently necessary to relieve fluid accumulations from a patient's internal body cavities. This is typically done by a naso-gastric tube which is inserted through the patient's nasal passages and into the patient's stomach. If the patient is confined to bed the tube is connected to a suction system which continually draws fluid outward through the tube and passes it through a drainage system to a collection point. Such a suction system is often constructed as a built-in fixture into each hospital room so that it may be made conveniently available for any patient needing it. During periods of patient transport or ambulation the naso-gastric tube is frequently left inside the patient, but disconnected from the suction source, and the end of the tube is clamped to prevent leakage. If the patient is transported with the tube clamped for very long, there is always the risk and possibility of aspiration due to the clamping of the naso-gastric tube. The clamping may lead to the patient regurgitating around the naso-gastric tube resulting in gastric fluids entering the patient's lungs, and subsequent pneumonia symptoms. For seriously ill patients, aspiration can result in increased morbidity or death due to complications such as these, and it is therefore extremely important to use careful judgment whenever a naso-gastric tube is clamped.

A preferable and alternate procedure to the foregoing involves disconnecting the naso-gastric tube from the suction source and immediately placing it into a collection reservoir whereby gastric fluids may continually drain regardless of the patient's movement. This has been inconvenient to accomplish, however, for the transport of a seriously ill patient usually involves the corresponding transport of a significant quantity of medical paraphernalia attached to the patient. The addition of yet another medical device further complicates the total transport problem, and as a result the naso-gastric tube is usually clamped.

SUMMARY OF THE INVENTION

The present invention provides a means for easily connecting the naso-gastric tube to a fluid-collection reservoir by simply fitting the tube over a specially constructed nozzle and pinning the collection bag to the patient's outer garments. The invention comprises a disposable, sealed bag and nozzle assembly wherein the nozzle is adapted for connection to a naso-gastric tube, and has an attached closure cap for sealing the nozzle whenever the bag is no longer used. The nozzle assembly includes an elongated base member having a narrowing taper which enables a sealable connection to a thin plastic bag by means of a heating process. The heating process melts the plastic material of the bag and the corresponding nozzle assembly material to bond them together to form a single structure, and the heating process is typically applied by means of an impulse-type heating element which is placed adjacent the bag and nozzle assembly. This type of heating element provides a seal across the entire bag and nozzle assembly, and eliminates any openings which might otherwise permit fluid leakage.

BRIEF DESCRIPTION OF THE DRAWINGS

A preferred embodiment of the present invention is described herein, and in conjunction with the appended drawings in which:

FIG. 3B illustrates the step of inserting the nozzle assembly into the bag end, and FIG. 3C illustrates the step of heat-sealing the combination.

DETAILED DESCRIPTION OF THE PREFERRED EMBODIMENT

Figure 1:
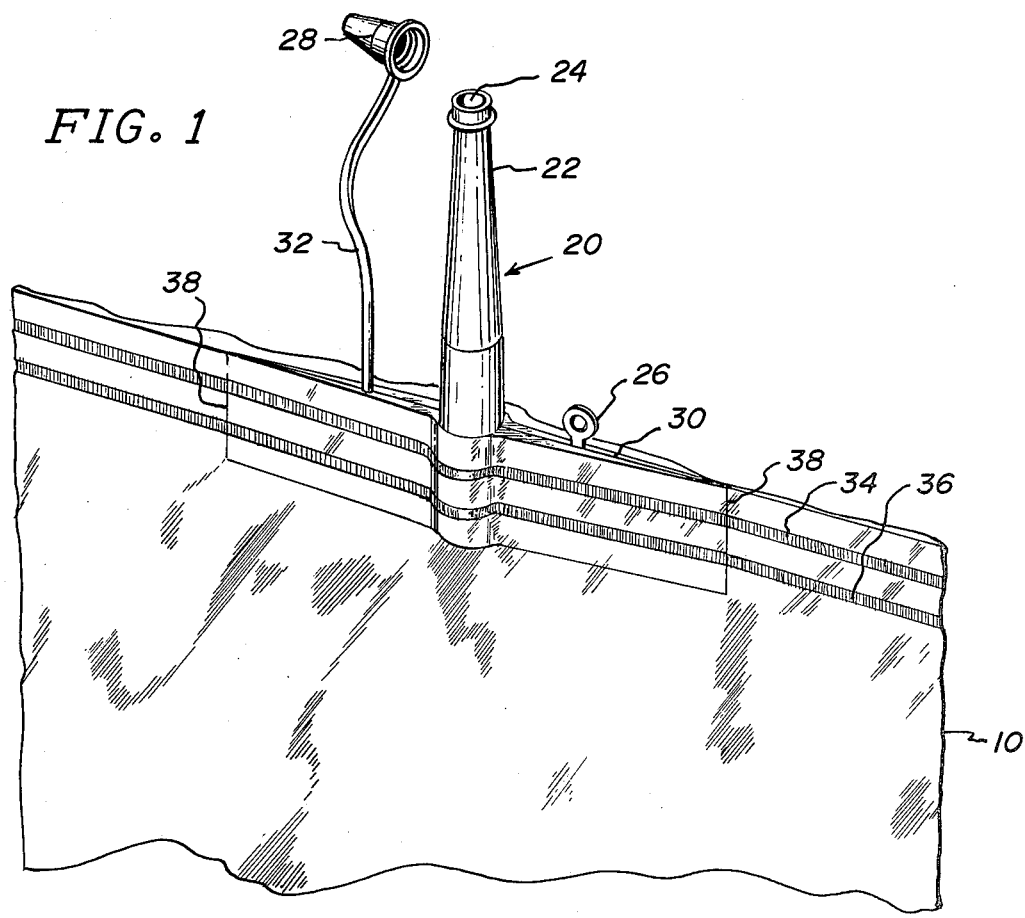
FIG. 1 illustrates a partial view of the invention in perspective side view.

Referring first to FIG. 1, the invention is shown in side view perspective. A thermoplastic bag 10 which forms a part of the present invention, has its lower end (not shown) sealed according to conventional plastic bag sealing procedures. The method of heat sealing may be accomplished through a heating process which is well known in the art. Bag 10 is typically formed from polyethylene plastic, preferably of a thickness from 2-8 mils. The top edge of bag 10 is initially open, but is sealed shut according to the teachings of the process of manufacturing the present invention.

A bag nozzle assembly 20, also constructed from polyethylene plastic, forms the second element of the present invention. Nozzle assembly 20 comprises a nozzle end 22 which has a taper terminating in an opening 24 which passes through the entire nozzle assembly and opens to the interior of bag 10. A loop 26 is formed along a base 30, to enable the attachment of the nozzle assembly and bag to a patient's outer garment. An end cap 28 is formed at the end of the plastic stem 32 projecting from base 30. Since stem 32 is flexible and may be easily deformed, end cap 28 may be brought into closing contact with opening 24, and provide a means for sealing the nozzle assembly from leakage. It is to be assumed that the interior of end cap 28, as well as the exterior end of nozzle 22, have formed thereon a mating sealing ring and groove so that end cap 28 may be snapped into place over opening 24. End cap 28 has an elongated shape to permit the present invention to be used with a naso-gastric suction tube having a second tube for venting. For example, a naso-gastric tube manufactured by Sherwood Medical Industries, Inc., St. Louis, Missouri under the trademark "Salem Sump" tube has a small vent tube passing internal the naso-gastric suction tube. This "sump" tube is brought out near the end of the larger tube and terminates in an outwardly expanding conical shape for coupling to a suitable connector. The elongated shape of end cap 28 is sized so as to be inserted into the "sump" tube opening and thereby provides a seal for this tube.

Base 30 and the upper edge of bag 10 are sealed together by means of a heat seal which extends across the entire upper edge of bag 10 after nozzle assembly 20 has been inserted into the bag end so as to bring base 30 and the upper edge of bag 10 into alignment. In the preferred embodiment a double heat seal 34 and 36 is used across the bag and base surface.

Base 30 has a thickness of approximately 3/16 inch near the lower end of nozzle 22, and tapers to an outer end 38 thickness which is approximately the thickness of bag 10. The reason for this taper is extremely significant to the invention, for it is difficult to obtain a sealing connection between a thin plastic membrane such as bag 10 and a heavy plastic component such as nozzle assembly 20. To apply the amount of heat necessary to bond the heavy plastic material is typically an excess of the heat which completely melts the thin plastic bag material. Further, at the point of discontinuity, where the edge 38 of nozzle assembly 20 terminates, the amount of heat necessary to obtain a bond between the bag 10 and nozzle assembly 20 must approximately equal the amount of heat necessary to bond the two sides of bag 10. Any significant difference in the heat relationship over the discontinuity created by edge 38 will either result in a poor bond between bag 10 and base 30 or will result in melting the material of bag 10 near the discontinuity. It is therefore crucial that the relative thickness of the total bonded package gradually diminish toward the point of discontinuity in order to create an effective seal over the region of discontinuity. The present invention solves this problem by use of the novel taper on base 30, together with the heating process selected for use with this invention.

Figure 2:
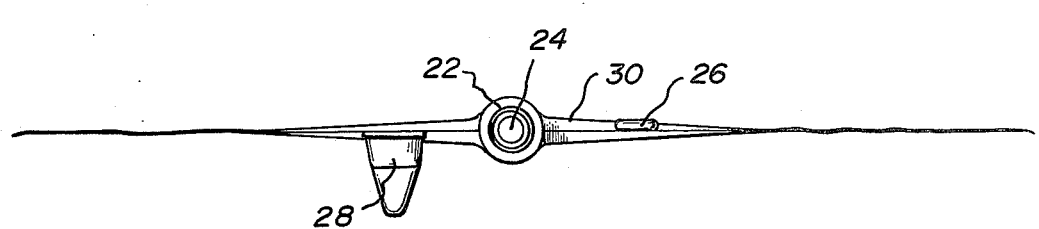
FIG. 2 illustrates the invention in top view.

FIG. 2 illustrates the invention in top view, showing the thickness configuration of base 30 as well as its taper as hereinbefore described. The entire nozzle assembly 20, including nozzle end 22, loop 26, base 30, and end cap 28 and stem 32 are formed from a single plastic injection molding process. This process comprises an important first step in the manufacture of the invention.

Figure 3A:
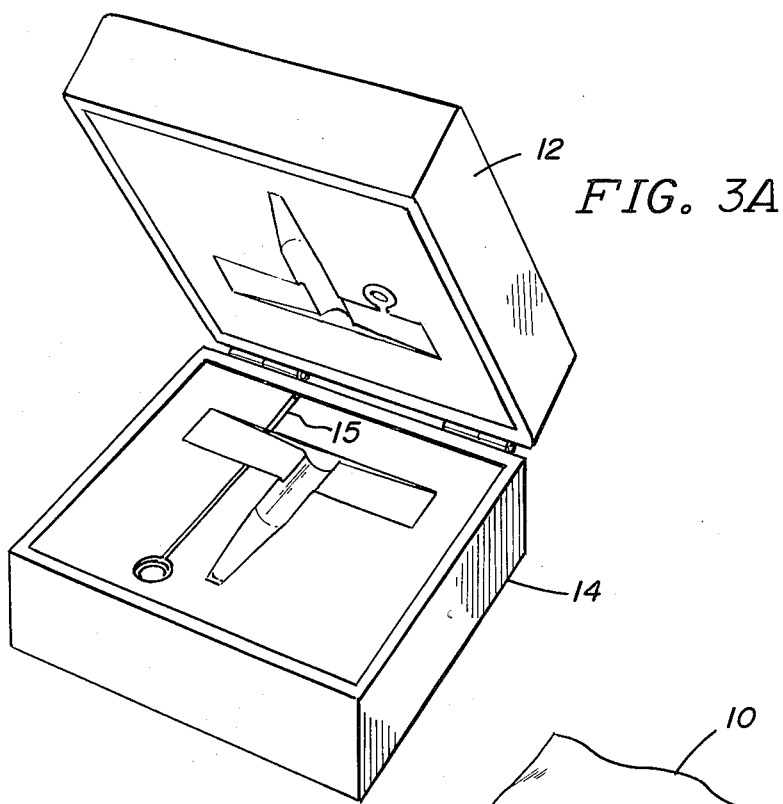
FIG. 3A-3C illustrate the process steps for forming the invention, wherein 3A illustrates the step of molding the nozzle assembly.

FIG. 3A illustrates a plastic mold wherein nozzle assembly 20 may be manufactured. The mold consists of two mold halves 12 and 14 having therein suitable cavities conforming to the shape of nozzle assembly 20. A plastic injection port 15 is provided for the high pressure injection of molten plastic material. Injection port 15 is positioned preferably opposite the position of stem 32, for the reason that plastic material must be injected along and through the cavity forming stem 32 which also forms end cap 28. By positioning injection port 15 in this manner, it is assured that sufficient material will be injected into the mold cavity to completely fill and form the components.

Figure 3B:
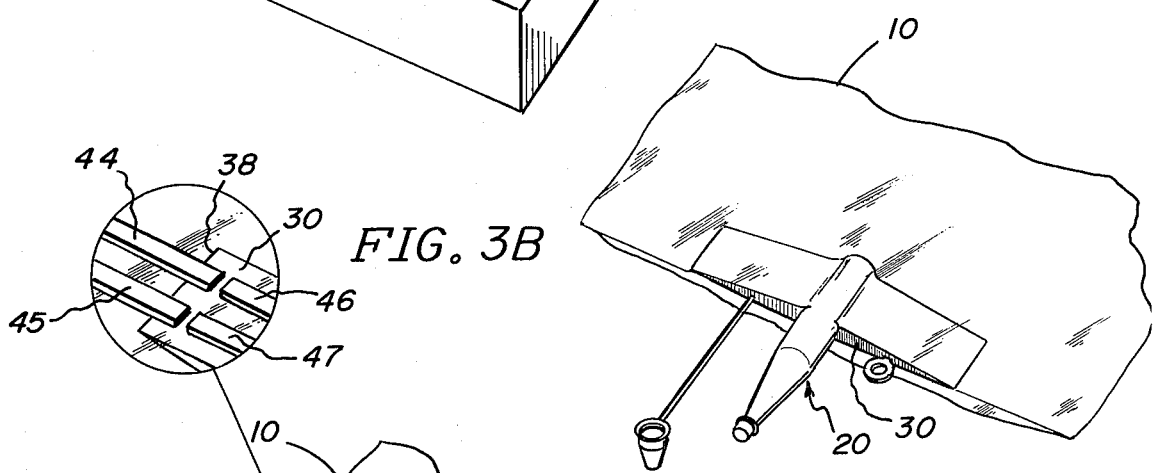

FIG. 3B illustrates a second step in the construction process, wherein nozzle assembly 20 is inserted into the open end of a bag 10. Nozzle assembly 20 is centered at the bag end, with base 30 aligned along the upper edge of the bag, and with an internal bag surface contacting each of the outside surfaces of base 30.

Figure 3C:
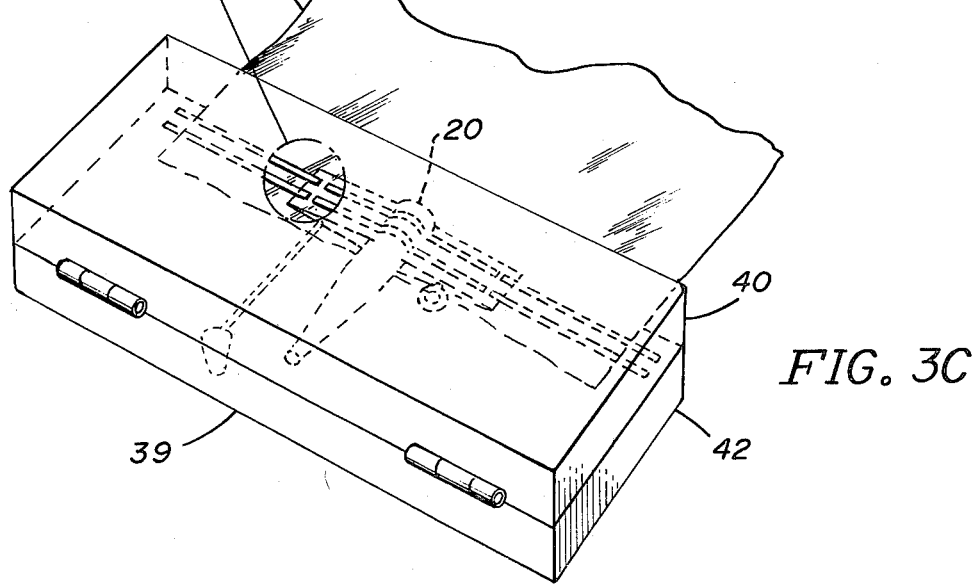

FIG. 3C illustrates the third and final step in the construction of the invention, wherein a heating element 39 is clamped over the bag and nozzle assembly for application of heat for sealing. Heating element top section 40 has an internal surface conforming to the shape of base 30, and heating element bottom section 42 has a similar internal shaped surface. A pair of parallel heating strips are preferably positioned along the respective internal surfaces of sections 40 and 42 for applying a double heat seal along the entire bag and base assembly. In the preferred embodiment it has been found desirable to provide a greater heating over the surface of base 30 and a lesser heating over the bag surfaces. This is accomplished by increasing the heating capacity of that portion of the heating element which contacts base 30 and reducing the heating capacity of that portion which contacts only bag 10. Theoretically it is desirable to construct a heat sealing member having a heat distribution pattern across the bag and nozzle assembly base which is inversely related to the total thickness of plastic material at every point. This can be accomplished through the careful design of the heating elements which are placed in sections 40 and 42. In the actual construction of these heating elements it was found sufficient to provide three heating element stages across the bag and base: two identical stages running from the respective edges of the bag to a point overlapping the base edge 38, and one stage running across the remainder and center portion of base 30. The center stage developed approximately twice the heating capacity of the respective end stages, with the result that a complete heat seal bond extended over the entire bag and base combination, which bond provided a liquid seal reliably in production quantities. An expanded view of the heating elements is shown on the circled portion of FIG. 3C. Parallel heating wires 44 and 45 extend from the edge of bag 10 to a point overlapping edge 38 of base 30. These heating wires have a heating capacity sufficient to bond the plastic thickness of bag 10. Parallel heating wires 46 and 47 extend substantially across the remainder of base 30 to a point short of the other edge of base 30. These heating wires have a heating capacity sufficient to bond bag 10 to base 30, which in practice was found to be approximately twice the heating capacity required for wires 44 and 45. A small space exists between the respective heating wire pair ends, but it has been found that sufficient heat is generated at the heating wire ends to completely bond and seal bag 10 to base 30. The significant discovery in the aforementioned construction is that the taper of base 30 at edge 38 enables a bond to be accomplished at this point of discontinuity by the same amount of heat as is required to seal the bag material itself.

By applying the teachings of this invention it has been found possible to obtain a reliable and complete seal across the entire bag opening in a manner which is repeatable for production purposes. In particular, the seal formed at the junction of edge 38 and bag 10 has been found to be reliable and continuous, so that no fluid leakage is present at this point of discontinuity. The invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A sealable plastic bag formed from two pieces of similar plastic material of substantially dissimilar thicknesses by the application of a heating and bonding process, comprising:
   (a) a nozzle assembly having an extended centrally positioned tapered nozzle opening and a passage extending from said nozzle opening through a base member, said base member having a center thick portion and tapered ends which diminish linearly from said thick portion to a predetermined thickness;
   (b) a plastic bag of wall thickness substantially equal to said tapered end predetermined thickness, said bag attached to said nozzle assembly base along its edge and by a heat sealing process which bonds adjacent plastic materials together;
   (c) an elongated stem integrally formed from said nozzle assembly material and having a length exceeding that of said extended tapered nozzle opening, and a cap on the end thereof, also integrally formed from said nozzle assembly material and sized for closure fitting over said nozzle opening; and (d) a loop integrally formed from said nozzle assembly material and extending from said base member.

2. A gastric drainage bag and nozzle assembly adapted for insertion into a tube, comprising:

a plastic bag having a first closed end, and having a second end;

a nozzle assembly constructed from plastic material of similar type to said bag, said nozzle assembly having a projecting tapered cylindrical end adaptable for inserting into a tube, and having a base member attached to said end and integrally formed therewith, said base member having extended linearly tapered ears which taper to the thickness of said bag aligned along said bag second interior end and heat-sealed in bonding attachment thereto;

a passage extending through said base member and said projecting cylindrical end;

an elongated stem projecting from said base member and integrally formed therewith, toward said projecting cylindrical end; and a cap member attached to the end of said stem and integrally formed therewith, said cap member sized for sealing capping over said projecting cylindrical end.

* * * * *